United States Patent
Spreizer

(10) Patent No.: US 8,684,731 B2
(45) Date of Patent: Apr. 1, 2014

(54) CAPSULE AND PISTON

(75) Inventor: Heinrich Spreizer, Ermatingen (CH)

(73) Assignee: Transcodent GmbH & Co. KG, Kiel (DE)

( * ) Notice: Subject to any disclaimer, the term of this patent is extended or adjusted under 35 U.S.C. 154(b) by 179 days.

(21) Appl. No.: 13/195,339

(22) Filed: Aug. 1, 2011

(65) Prior Publication Data

US 2012/0028217 A1 Feb. 2, 2012

(30) Foreign Application Priority Data

Jul. 30, 2010 (DE) .......................... 10 2010 036 782

(51) Int. Cl.
*A61C 5/04* (2006.01)

(52) U.S. Cl.
USPC .......................................................... 433/90

(58) Field of Classification Search
USPC ........... 433/89, 90, 80; 206/219, 221; 604/87, 604/200, 218, 219, 221, 222, 225, 230, 311
See application file for complete search history.

(56) References Cited

U.S. PATENT DOCUMENTS

| | | | | |
|---|---|---|---|---|
| 2,381,785 A | * | 8/1945 | Thompson | 433/90 |
| 4,963,093 A | * | 10/1990 | Dragan | 433/90 |
| 5,083,921 A | * | 1/1992 | Dragan | 433/90 |
| 5,122,057 A | * | 6/1992 | Discko, Jr. | 433/90 |
| 5,172,807 A | * | 12/1992 | Dragan et al. | 206/219 |
| 5,322,440 A | * | 6/1994 | Steele | 433/90 |
| 5,460,523 A | * | 10/1995 | Schulman | 433/90 |
| 6,503,084 B2 | * | 1/2003 | Evers et al. | 433/226 |
| 6,877,983 B1 | * | 4/2005 | Dragan et al. | 433/90 |
| 2005/0147939 A1 | | 7/2005 | Zumkeller | |

FOREIGN PATENT DOCUMENTS

DE 10218859 A1 11/2003

* cited by examiner

*Primary Examiner* — Manuel Mendez
(74) *Attorney, Agent, or Firm* — Kolisch Hartwell, P.C.

(57) ABSTRACT

A capsule for receiving and delivering high-viscosity dental materials has a housing which defines an interior chamber. The housing and the interior chamber have a first section, a transition area, and an exit nozzle. The interior chamber of the transition area tapers continuously towards its second end. The interior chamber of the transition area is defined by the outer surfaces of an oblique truncated cone with an opening angle of approximately 55°.

21 Claims, 7 Drawing Sheets

CAPSULE AND PISTON

CROSS-REFERENCE TO RELATED APPLICATION

This application claims priority to German Patent Application No. 10 2010 036 782.6, filed Jul. 30, 2010, which is hereby incorporated by reference.

BACKGROUND

Capsules may be used for receiving and dispensing high-viscosity materials. Various application areas utilize high-viscosity materials, e.g., dental technology. The composite materials have a high filler content and thus high sagging resistance and plasticity.

The aforementioned materials are dispensed in units of, e.g., quantities of 2 g to 5 g. Smaller amounts, such as 250 mg to 350 mg, are dispensed in standardized disposable plastic packaging, e.g., in capsules or tips.

To an extent depending on the composite material, during use, very high expression pressure can arise in the capsule and very large expression forces at the dosing pliers. While low expression pressure makes for highly dependable use as the capsules cannot rupture, users such as dentists require a long and slender dosing channel for convenient application. For precision handling, the lowest-possible expression forces are advantageous. Between these requirements, an optimized solution needs to be found.

SUMMARY

Proceeding therefrom, an object of the present disclosure is to provide a capsule and a piston for dispensing high-viscosity materials, such as dental materials, that will facilitate dispensing at reduced expression pressure and low separation of the dispensed material combined with low dead volumes. This object is achieved by embodiments of the current disclosure.

The present disclosure relates to a capsule for receiving and dispensing high-viscosity materials, such as dental materials, comprising a housing, said housing defining an interior chamber and an opening for introducing a piston and a discharge opening, and wherein the housing comprises the following sections: a first housing section which defines a first cylindrical interior chamber section, said first housing section having a first central longitudinal axis, a first end and a second end; a second housing section which forms an exit nozzle, wherein the second housing section has a second central longitudinal axis, a first end and a second end, and the second housing section defines an exit channel that opens into the opening formed at the second end; and a transition section whose first end is connected to the second end of the first housing section, and whose second end is connected to the first end of the second housing section; wherein the first central longitudinal axis and the second central longitudinal axis intersect at an angle $\alpha$. In addition, the present disclosure relates to a piston, in particular for expressing material from said capsule.

An embodiment of a capsule for receiving and dosing high-viscosity materials comprises a housing, said housing defining an interior chamber and having one opening for inserting a piston and one delivery opening, and wherein the housing comprises the following sections: a first housing section which defines a first, especially cylindrical, interior chamber section, said first housing section having a first central longitudinal axis, a first end and a second end; a second housing section which forms an exit nozzle, wherein the second housing section has a second central longitudinal axis, a first end and a second end, and the second housing section defines an exit channel that opens into the delivery opening formed at the second end; and a transition section whose first end is connected to the second end of the first housing section, and whose second end is connected to the first end of the second housing section; wherein the first central longitudinal axis and the second central longitudinal axis intersect at an angle $\alpha$ of 40° to 50°, preferably 45°. The transition section tapers from its first end to its second end, and the taper angle $\beta$ is at least 50° to 90°.

The proposed geometry reduces the necessary expression pressure because the geometry of the interior chamber promotes flow. The resistance to flow during expression of dental materials is reduced. Due to the lower expression pressure, the exit channels can be of smaller diameter. That reduces material loss during application. Furthermore, the time and the effort required for delivering the dental materials are reduced. The force required for expression, for example, could be reduced by 20-30%.

Candidate materials for the capsule are plastics such as PE, in particular PA, PBT, POM, etc.

For the sake of improvements, the internal contours of the capsules were optimized. The advantages are attributable mainly to the relatively steep taper angle $\beta$. The transition also reduces the tendency of high-viscosity materials to separate. Apparently, high-viscosity dental materials have lower flow resistance when transitioning from a large inner diameter to a small inner diameter by means of a truncated cone.

The lower limit for the taper angle is 50°. Smaller angles significantly impair the properties of the capsule. Smaller cone angles cause a significant increase in the flow resistance.

A further advantage of this geometry is ease of manufacture. A first cylinder core having a truncated cone transition, and a nozzle core having a right-angled contact surface with the truncated cone have no undercuts. The structure can thus be produced or demolded with two cores.

The angle $\alpha$ between the first and second central longitudinal axes is preferably between 10° and 80°, especially between 30° and 60°, especially preferably between 40° and 45°.

Preferably, the transition section tapers in the form of an oblique truncated cone, with the taper angle $\beta$ corresponding to the opening angle of the cone. In oblique cones, the tip is located away from the perpendicular straight line through the center of the circular base. The use of an oblique truncated cone (with a large opening angle) in the transition area is necessitated by the angle $\alpha$ between the first and second axes.

The oblique truncated cone can be arranged such that it is tilted at an angle $\gamma$ relative to the first central longitudinal axis, with the angle $\gamma$ being especially 10° to 20°. This allows a piston to penetrate deeper into the transition section, thereby reducing the amount of non-recoverable material (material loss).

In particular, the transition section connects the first interior chamber section to the exit channel, wherein the transitions can be continuous between the first interior chamber section and the interior chamber of the transition section, and between the interior chamber of the transition section and the exit channel, respectively. In some embodiments, the transition section connects the first interior chamber section to the exit channel, wherein the transition between the transition section and the exit channel has a wall piece that is arranged transversely to the flow direction of the filler material. In this way, a flow edge is formed.

In particular, the wall piece can be of an annular design and arranged perpendicularly to the second central longitudinal axis.

The diameter (d) of the interior chamber of the transition section preferably decreases steadily from the first end to the outer boundary of the wall piece and at a constant slope.

The second housing section can connect to the transition section via the wall piece.

The transition between the transition section and the exit channel can have a flow edge. On passing the wall section or flow edge, the material undergoes a microscopic change. Due to the shear stress, the molecular chains become partially "uncoiled" or disentangled and become oriented in the flow direction, that is, their cross-links are dissolved. As a result, the viscosity in the boundary layer changes and causes positive flow behavior in the nozzle. After the flow pressure has been dissipated, the macromolecules then become entangled or coiled or entwined again. Separation of the filler material after it leaves the nozzle does not occur. With the help of the flow edge, a further clearly measurable reduction and calming of the expression force is achieved. The flow behavior is steady and continuous, without marked fluctuation in expression force.

The diameter (d1) of the first interior chamber section is especially larger than the diameter (d2) of the exit channel. In the outside area of the first end of the first housing section, a flange can be formed. This is usually annular.

Preferably, the diameter (d) of the interior chamber of the transition section decreases steadily and at a constant slope from the first end to the second end. The slope can be calculated from the taper of the transition area.

In some embodiments of the present disclosure, the transition section is a direct continuation of the first housing section, and the second housing section is a continuation of the transition section either directly or via the aforementioned transverse wall piece.

The housing wall can be reinforced in the area of the transition section. For expression of the material from the capsule, there are standardized expression tools on the market. Consequently, the outer contour of the collar and the bore are largely determined. As increasingly harder materials are to be delivered, the tools are increasingly being supplied in larger translations. This increases the load on the capsule during expression. Typically, a conventional capsule ruptures in this regard at the transition area to the nozzle. Here, too, is where the highest forces arise, and the cross-section is weakened by the exit channel. During optimization of the base, it was calculated that a reinforcement of about 30% to 50% provides a sufficient increase in strength. The reinforcement is provided on the outer surface of the transition area.

Preferably, the taper angle $\beta$ is between 50° and 120°, especially between 50° and 70°. More obtuse angles are less deleterious than more acute angles.

The exit channel is preferably cylindrical. In a further embodiment, the exit channel can be formed as a cone, which opens at an angle of 1° to 3° relative to the nozzle outlet opening.

The first diameter (d1) is especially at least twice as large as the second diameter (d2). Thus, the ratio d1/d2 can lie in the range 2.0-4.0 for example.

The object is also achieved by providing a piston, which has an end face facing the exit channel and a scraper edge or lip, wherein one transition surface of the end face, which is contiguous with the scraper edge, forms an angle ($\delta$) of 90° to 120° with the longitudinal axis of the piston, wherein the angle ($\delta$) is arranged such that, in the intended thrust direction for delivery of the filler material, the outward transition surface runs obliquely rearwards. The term "outward" refers to a direction from the longitudinal axis of the piston towards the inner walls of the capsule, the term "rearwards" means a direction opposite to the intended thrust direction of the piston relative to the capsule for dispensing the material. With the help of the piston, the filler material is scraped from the capsule inner wall during the delivery process, without jamming against it.

The angle ($\delta$) is especially between 105° and 120°.

At the scraper edge or lip is formed in particular at least one elevation (defined as a projection or rib, which extends preferably in the longitudinal direction of the piston).

The piston can be made from a semi-elastic material, which presses against the cylinder wall under high pressure. The pressure deforms the piston such that an adequate seal and stability are created between the contact surface and the cylinder inner wall for the material to be delivered. The contact surface of the piston may also be coated to increase lubricity.

In some embodiments, the piston is made of a relatively stiff and/or hard plastic to prevent jamming or wedging with the inner wall of the capsule.

The piston can have at least one scraper lip, wherein at least one elevation is formed at the scraper lip. The elevation is arranged on the outer circumference of the scraper lip and creates a small gap for venting between the inner wall of the capsule and the scraper lip.

The piston can be symmetrical and have two sealing and scraper lips. Each lip has three elevations on its outer circumference. As a result, the air between composite material and piston can escape rearwards. On expression of the dental material, the capsule is free of air.

The object is also especially achieved by a combination of the capsule and the piston of the present disclosure.

In this regard, a gap, e.g., 20 μm to 50 μm wide, can be especially formed between the scraper edge and the inner wall of the first section. In this way, there is no pre-tension between the edge 511a or 511b and the inner wall of the piston. In addition, air can escape through the gap (venting).

The formation of dead corners and volumes is avoided in a combination of the capsule and the piston of the present disclosure, as the volume of the transition area is relatively small due to the large taper angle. The residual amount of material in the capsule after delivery (which is composed of the residual material in the three areas of the capsule) is to be regarded as the loss amount. Since the materials to be delivered can be very expensive, the lowest residual amount is sought. The piston fulfills two functions in this regard, namely scraping the dental material off the wall and maximum possible penetration into the cone. As, in the case of the present capsule, the volume of the transition area is small due to the obtuse taper angle, the residual amount of material remaining therein is low too. The residual amount is thus determined by the residual amount in the nozzle, which is defined by the nozzle length and nozzle diameter.

Moreover, within the scope of the present disclosure, there is no need to use a cone-shaped piston to deliver as much of the material as possible from the capsule. The use of cone-shaped pistons having a conical end face namely causes material to accumulate and adhere between the inner wall of the capsule and the piston. The combination of the capsule and the piston of the present disclosure is therefore also advantageous with respect to the avoidance of additional friction during delivery.

Overall, a lowering of the resistance between the piston and cylinder is achieved. To the very high pressures or flow forces that arise in the capsule during dosing must be added the resistance between piston and capsule. When the material is being expressed, all the resistance must be overcome. This resistance can be very high if the geometry is poor. Conventional pistons with steep, cone-shaped end faces can generate very high frictional forces, because the material becomes wedged between the piston cone and the cylinder wall. Separation can then occur. This lowers the quality of the product on one hand and, on the other, the piston sticks in the capsule.

As described, these drawbacks are overcome by the present teachings. In some embodiments, the end face of the piston forms a right angle or a negative angle, e.g., −10° to −30° in the area of contact with the capsule inner wall. This means that an acute angle of less than 90° is formed between the capsule wall and the piston. The edge area of the piston end wall, expressed in terms of the delivery direction, is obliquely rearwards. As a result, the material is scraped cleanly from the wall. Only the sliding friction between piston and cylinder needs to be overcome. Adhesive effects or separation do not occur. The resistance can be optimized by using suitable materials for capsule and piston and/or by coating the piston, at least in the contact area. Candidate coating materials include a Teflon® dispersion or a Teflon® admixture to the piston material.

Protection is also sought for a process for manufacturing embodiments of capsules and/or pistons of the present disclosure. The parts are injection molded, with two cores being used for capsule production, namely a first core for the cylindrical exit nozzle and a second core for the first interior chamber section and the truncated cone-like transition area. The feasibility of this approach is ensured by the fact that there is no back molding between the two cores. The cores contact each other at right angles without undercuts. Lateral forces do not occur. Provision is made for a shift in tolerance in that, in the transition area, the diameter of the conical section (the second end of the transition region) is made greater than the diameter of the nozzle by a predetermined amount (e.g., 0.2 mm to 0.5 mm).

Protection is sought for any new combinations of the features of the present disclosure.

BRIEF DESCRIPTION OF THE DRAWINGS

Further characteristics and advantages of the present disclosure will become apparent from the following description of one or more embodiments illustrated in the accompanying drawings.

DETAILED DESCRIPTION

Figure 1:
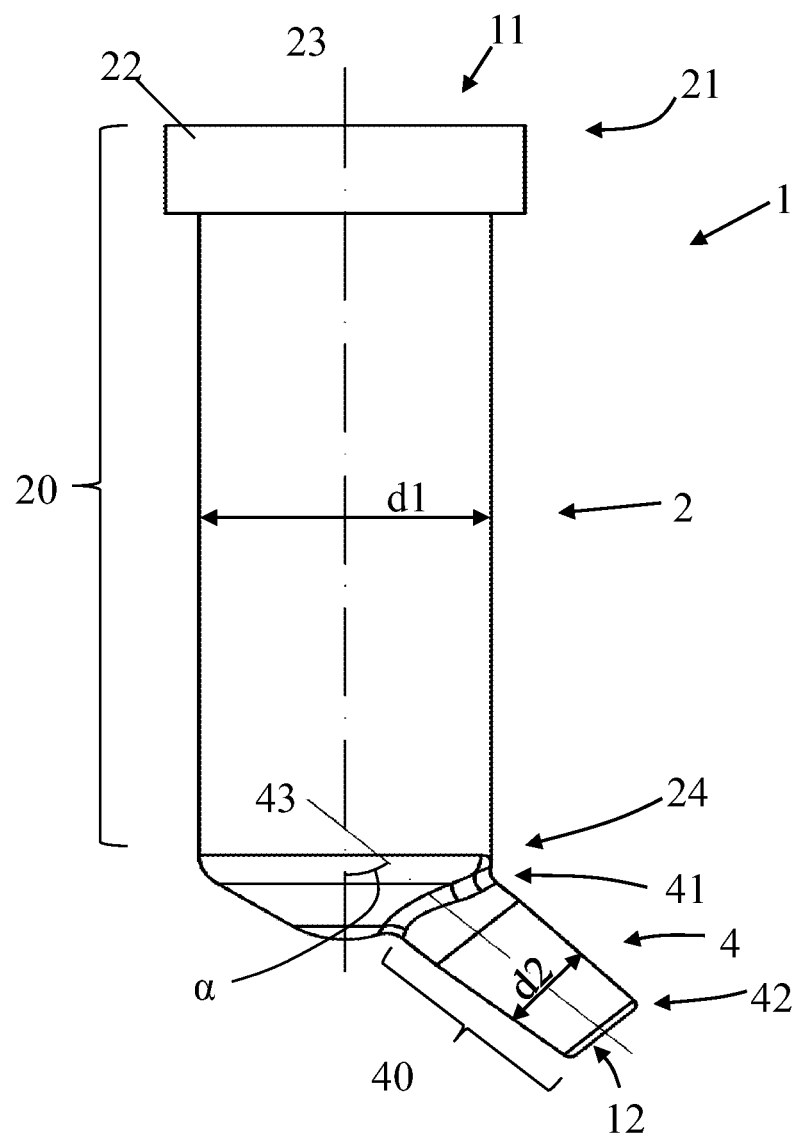
FIG. 1 illustrates a plan view of an embodiment of a capsule.

FIG. 1 shows an embodiment of a capsule 1 for receiving and delivering high-viscosity dental materials. The capsule 1 can be made of plastic.

The capsule has a housing that defines an interior chamber. The housing comprises on one end a first opening 11 for inserting a piston (not shown), and on the other a second opening 12 which serves as a delivery opening to permit the dental material to exit, when the piston is pressed into the interior chamber through the first opening.

The housing and the interior chamber have a first section 2, a transition area 3 and a second section 4 (exit nozzle).

The first section 2 comprises a first housing section 20, at the first end 21 of which is formed the first opening 11 of the capsule 1. At the first end of the first housing section 20 is also formed an outwardly extending flange 22 which in particular extends radially around the edge of the opening 11. The interior chamber of the first housing section 20 is essentially cylindrical and of a circular cross-section, constant diameter d1, and has a first central longitudinal axis 23. The second end 24 of the first housing section 20 is connected directly to a first end 31 of the transition area 3.

The second end 32 of the transition area opens into the second section 4, which is designed as a cylindrical exit nozzle having a second central longitudinal axis 43. The inner diameter d2 of the second section 4 is constant and smaller than the inner diameter dl of the first section 2. Whereas the first end 41 of the housing 40 connects directly to the transition area 3, the second end 42 has the outlet opening 12.

The first central longitudinal axis 23 and the second central longitudinal axis 43 form an angle α of about 45°.

Figure 2:
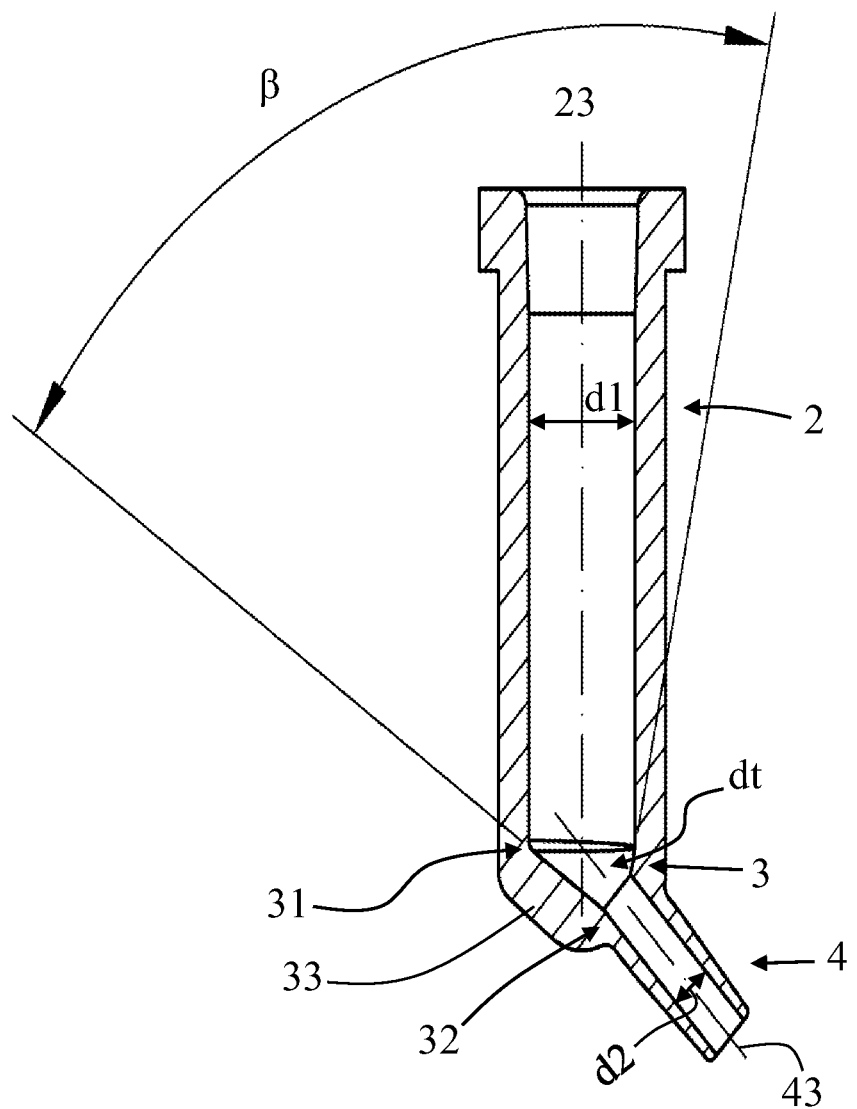
FIG. 2 illustrates a first cross-sectional view of the capsule of FIG. 1.

As is evident from FIG. 2, the interior chamber of the transition area 3 has an inner diameter dt, which steadily tapers or decreases towards its second end 32. The diameter dt at the first end 31 corresponds to the diameter d1 of the first housing section 20. The diameter dt, which varies along the transition area 3, matches at the second end 32 the inner diameter d2 of the second housing section 40. The taper is continuous, and (within the transition area 3) has a constant slope. This means that the interior chamber of the transition area 3 is limited by the outer surface of a truncated cone. The cone corresponding to the truncated cone is an oblique cone having an opening angle β, which corresponds to the taper angle. The opening angle β in this example is approximately 55°. Thus, the taper may be relatively steep, which surprisingly leads to lower expression forces in the interior chamber combined with constant delivery times and to less separation of the dental material.

The line indicated by 32 is where the two cores employed in production by injection molding meet each other.

A region of thicker material 33 in the area of that housing wall which intersects the first longitudinal axis 23 provides the necessary stability to accommodate the high loads during delivery of the material.

Figure 3:
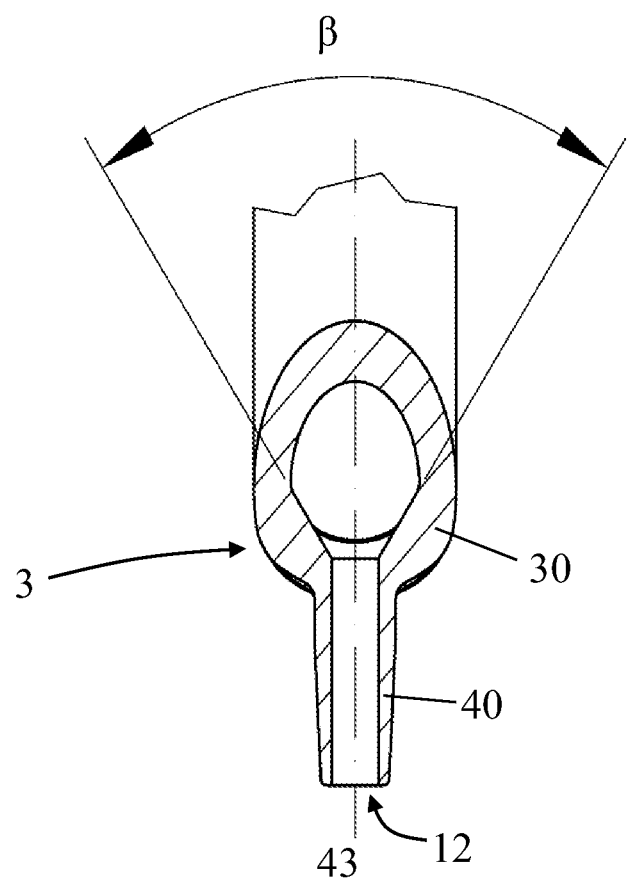
FIG. 3 illustrates a second cross-sectional view of the capsule of FIG. 1.

FIG. 3 is a further cross-sectional view. The cross-section extends through the exit nozzle 2 and the transition area 3. The interior chamber of the transition area 3 (defined by the wall 30) opens under a taper angle β into the wall 40 defined by the exit channel.

By means of the present disclosure, an improvement in flow characteristics in combination with a reduced tendency to separate can be achieved. This means that, when high-viscosity materials are being dosed, the dosing forces can be lowered substantially compared to conventional nozzles, i.e., lower forces are required in use, as a result of which the force for dosing can be reduced.

Figure 4:
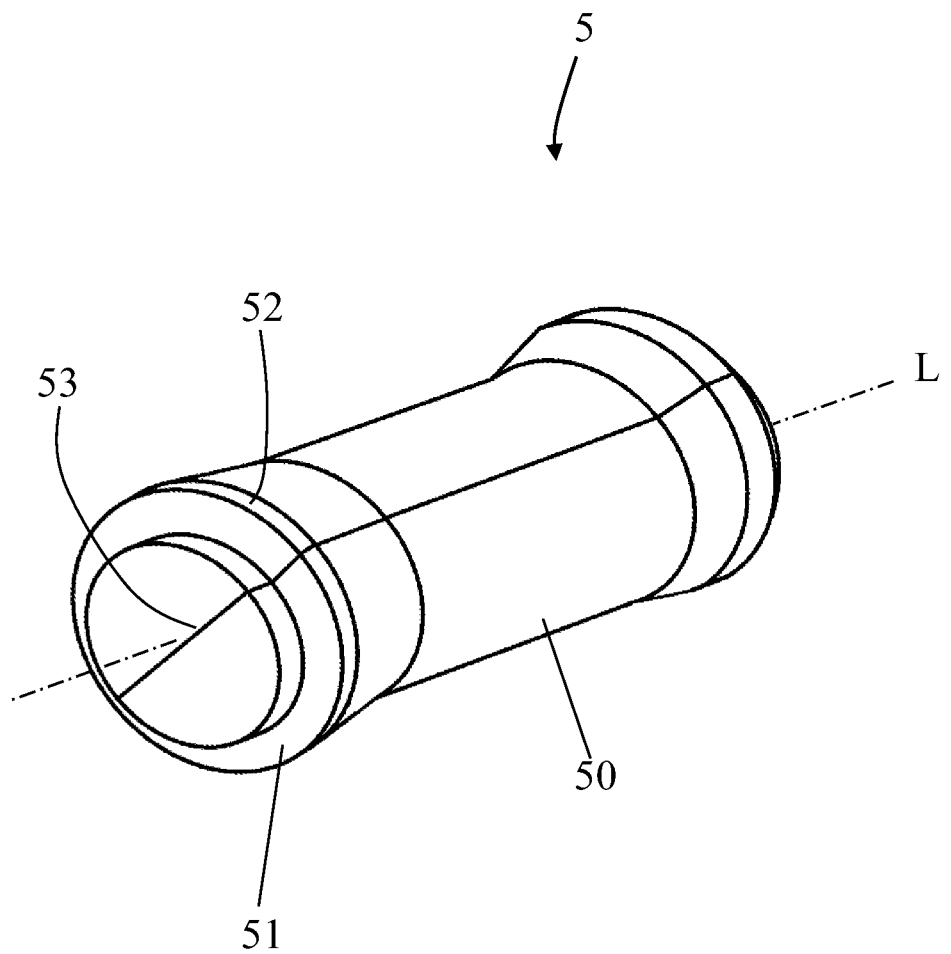
FIG. 4 illustrates a perspective view of an embodiment of a piston.

FIG. 4 shows an embodiment of a ram/piston 5 for delivery of dental material, for example, from a capsule 1 as described herein. For this purpose, the plunger 5 is inserted into the first opening 11 and pressed down towards the exit nozzle 4. Due to the reduction in volume, residual air escapes rearwards at first; thereafter the material flows out from the outlet opening 12.

The ram 5 can be manufactured from plastic. It has a base body 50 having an end face 51, which is introduced into the interior chamber of the capsule first. The end face 51 forms a right angle with the inner wall of the capsule or the end wall forms an acute angle of less than 90° with the capsule wall, that is, a negative angle of −10° to −30° is present. As a result, the material is scraped cleanly from the wall. Essentially, only the sliding friction between the piston 5 and the inner wall of the cylinder needs to be overcome. Adhesive effects or separation are avoided. The resistance can be optimized by coating the piston, in particular in the area of the contact surface/edge 52. Overall, the resistance between the piston and cylinder inner wall is reduced.

During automatic insertion of the piston 5 into the capsule opening 11 and expression of the materials, air from the trapped interior chamber of the capsule must be able to escape rearwards. In this regard, the material to be delivered may not escape rearwards towards the first opening 11, as contamination of the plunger of the expression pliers must be avoided. For this reason, the piston body 50 is formed with a venting gap 53, which is large enough for air to escape safely, but cannot be permeated by the high-viscosity material to be delivered.

Overall, the piston 5 is symmetrical, has two outwardly projecting sealing and scraping edges or lips 52, which exert low friction on the walls of the capsule. The piston 5 has two sealing and scraper lips.

Figure 5:
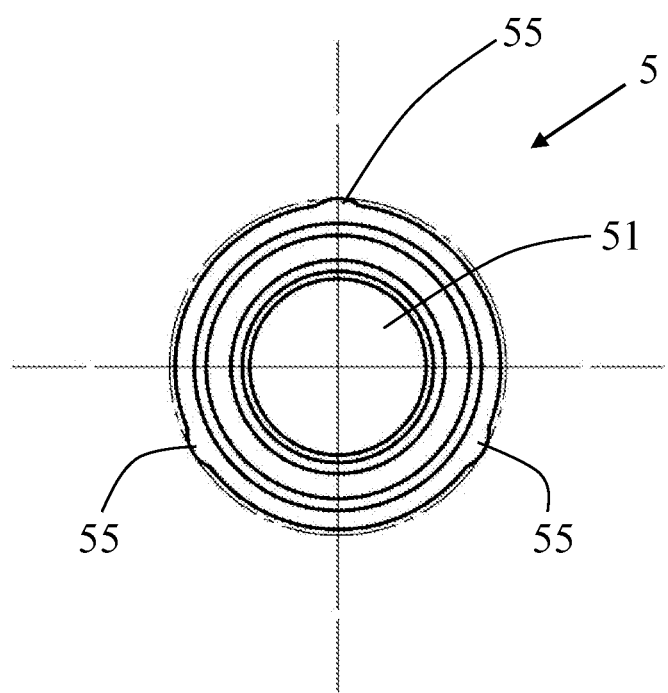
FIG. 5 illustrates a plan view of the end face of another embodiment of a piston.

FIG. 5 is a plan view of end face 51 of another embodiment of piston 5, which is the same as the piston of FIG. 4, except that piston 5 in this embodiment (at each of both sealing lips) has three elevations 55, which increase the frictional resistance with the capsule walls by about 3% to 5%. This force is not perceptible in application, but it ensures that the piston is held securely in the capsule and (especially during packaging) is not lost. However, the gap which the elevations create between the capsule wall and the sealing edge is so small that, although venting is possible, i.e., air can move between the sealing lips, the dental material cannot pass through the gap.

Figure 7:
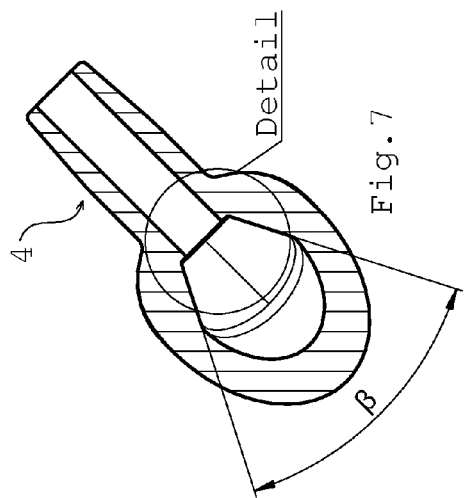
FIG. 7 illustrates a second cross-sectional view of the capsule of FIG. 6.
Figure 8:
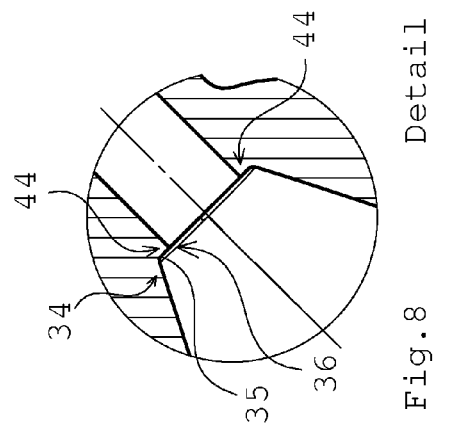
FIG. 8 illustrates a detail of the capsule of FIG. 6.
Figure 6:
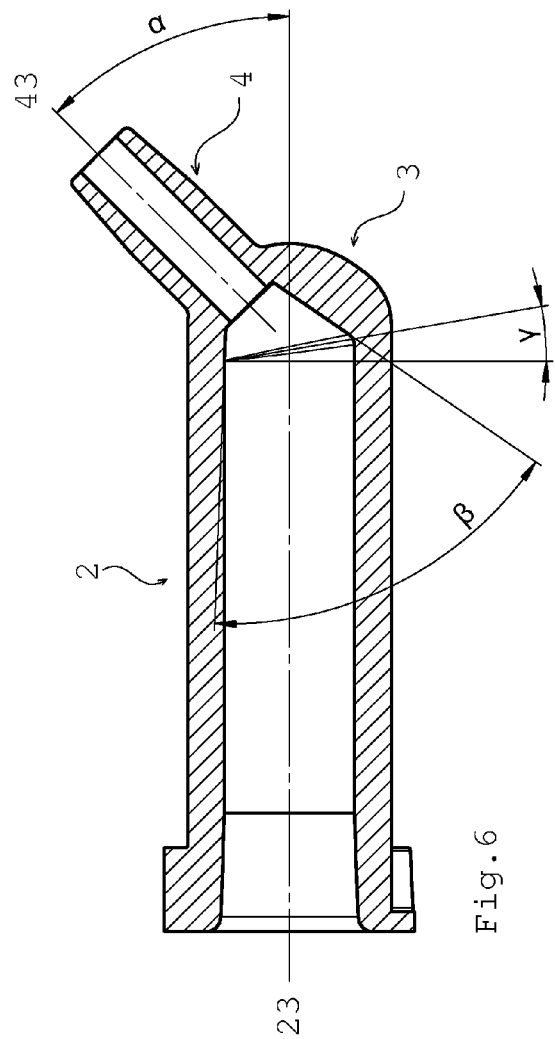
FIG. 6 illustrates a first cross-sectional view of another embodiment of a capsule.

A further reduction in expression forces is achieved with embodiments of the capsule, such as the embodiment shown per FIGS. 6, 7 and 8.

The capsule is basically constructed like the capsule shown and described in FIGS. 1 to 3. Corresponding components are therefore labeled with the same reference numerals as in the previous embodiment.

The angle α between the first central longitudinal axis 23 and the second central longitudinal axis 43 is about 45°. The transition area 3 corresponds to a truncated cone. A corresponding oblique cone has an opening angle β=55°, which corresponds to the taper angle.

At the transition 34 between the transition area 3 and the exit nozzle 2, which is particularly apparent in the detailed illustration in FIG. 8, there is a wall piece 35. The wall piece 35 is an approximately annular wall section, preferably 0.1 mm to 0.25 mm in width. The wall piece 35 is perpendicular to the flow direction or to the longitudinal axis 43 of the second section 4 (exit nozzle) and acts as a kind of baffle. The annular wall section connects on one end to the cone-shaped area of the transition area 3 and on the other to the first end 41 of the housing 40 of the second section 4. The part 44 of the housing 40 which forms the annular wall section forms a kind of projection for the filler material flowing into the exit nozzle 4. The transition edge or flow edge 36 between the annular wall section 35 and the second section 4 is sharp.

On passing the wall section 35 or flow edge 36, the material undergoes a microscopic change. Due to the shear stress, the molecular chains become partially "untangled" and oriented in the flow direction, that is, their cross-links are dissolved. As a result, the viscosity in the boundary layer changes and causes positive flow behavior in the nozzle. After the flow pressure has been dissipated, the macromolecules start becoming entangled and coiled again. Separation of the filler material after it leaves the nozzle does not occur. With the help of the flow edge 35, a further clearly measurable reduction and calming of the expression force is achieved. The forces are not subject to major fluctuations, i.e., the curve is continuous. The flow behavior is steady and continuous, without marked fluctuation in expression force.

In a further modification of the first embodiment, the cone-shaped section of the transition area 3 has been tilted relative to the first section 2. In this embodiment, the cone is tilted towards the second longitudinal axis 43. The angle γ of tilt here is 10°. The flow is not affected by the tilt. In each of the embodiments, residual material remains in the capsule during expression, depending on the piston and the truncated cone shape. In the present embodiment, this residual material can be reduced as, through the tilting, the piston can penetrate further into the cone-shaped transition area 3. Material loss during a delivery process can thus be reduced by about 30%, with the material loss in the nozzle remaining unchanged relative to the first embodiment.

Figure 9:
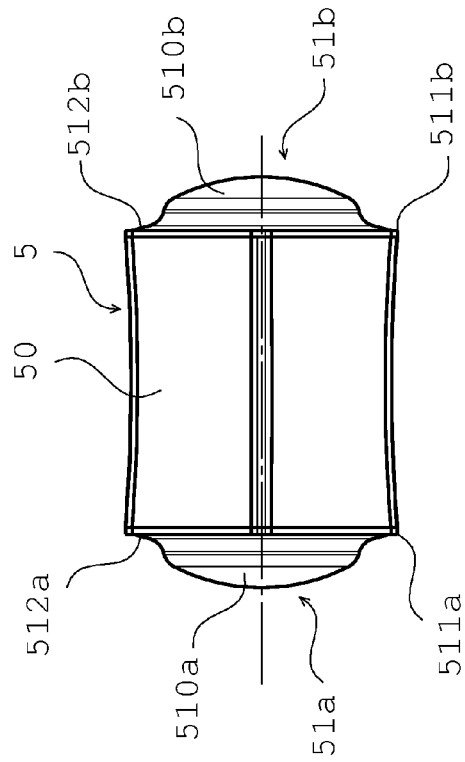
FIG. 9 illustrates a perspective longitudinal view of another embodiment of a piston.

FIG. 9 shows another embodiment of a piston 5. Unless otherwise described, piston 5 corresponds to the previously described embodiments. Corresponding components are therefore labeled with the same reference numerals as in the previous embodiments.

The piston 5 has a base 50 with a front end face 51a and a rear end face 51b. The piston 5 is symmetrical with regard to the front and rear areas. The end faces 51a or 51b each have a concave projection 510a or 510b.

The piston 5 can be made of a relatively hard plastic. In contrast to the first and second embodiments, the end faces 51a or 51b are each bounded by a circular scraper edge 511a or 511b, which has a radius such that, between the inner wall of the capsule and the scraper edge 511a or 511b (at least when the piston is not loaded), there is a gap, e.g., 20 μm to 50 μm. In this way, there is no pre-tension between the edge 511a or 511b and the inner wall of the piston. The conditions (as in the boundary layer) are such that expression forces can be reduced and jamming prevented. In addition, air can escape through the gap (venting). The filler material is scraped from the inner wall of the capsule by the piston 5.

Between the projection 510a or 510b and the respective edge 511a or 511b is arranged a transition area 512a or 512b. This is essentially annular but runs with a negative slope towards the edge 511a or 511b. This means that the surface 512a or 512b, when seen from a plan view of the respective end face 51a or 51b falls away outwardly towards the edge 511a or 511b. This is shown very clearly in FIG. 10, in which the negative slope of the surface 512a is indicated. The angle δ is a measure of the outward slope or the gradient of the surface 512a. The angle δ is preferably about 105° to 120°.

Figure 10:
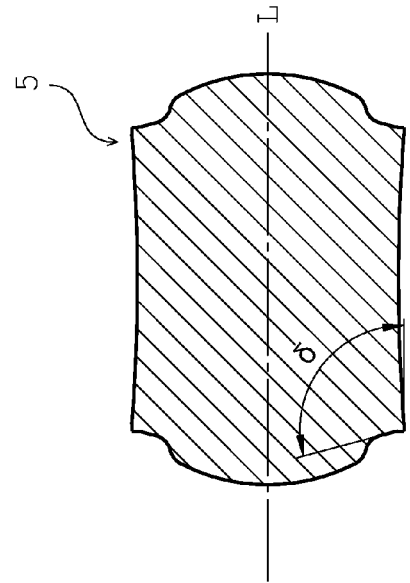
FIG. 10 illustrates a longitudinal section through the piston of FIG. 9.

From FIG. 10, a further characteristic of the piston 5 becomes clear. Due to the shrinkage of the plastics, the injection molding process can be designed such that the cylinder radius along the longitudinal axis L decreases towards the center in a controlled manner by approx. 0.2 mm. This means that the piston has a concave cylinder surface in the longitudinal direction. As a result, undesirable jamming of the piston 5 in the capsule is prevented.

Figure 11:
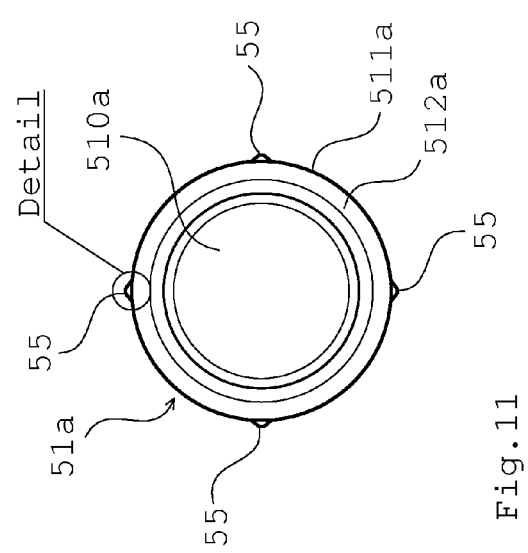
FIG. 11 illustrates a front plan view of the piston of FIG. 9.
Figure 12:
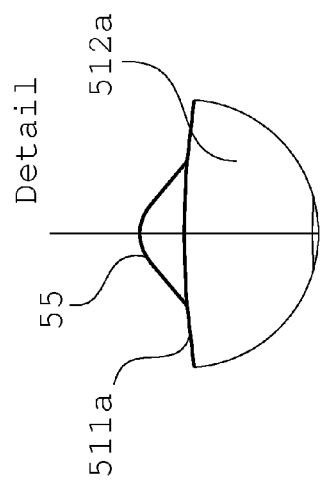
FIG. 12 illustrates a detail from FIG. 11.

FIGS. 11 and 12 show another characteristic of an embodiment of the piston 5. This characteristic can, but need not, be part of an embodiment of piston 5.

At the circumference of the outer wall of the piston 5 are formed projections or ribs 55. These overlap the capsule by approx. 0.1 mm to 0.2 mm. The piston is thus held firmly when inserted into the capsule, and cannot fall out or be pulled out. Tolerances can be reliably compensated by the projections, and the piston 5 is held in the capsule with reproducible forces. The piston is clamped to the capsule via the projections 55. However, as the forces exerted amount to only about 3% to 5% of the expression forces, this additional force is not perceptible to the user during delivery. On the other hand, during transporting or packaging, the pistons cannot be lost because they are held securely in the capsules.

Three to six ribs can be attached, depending on the capsule and piston material and on the behavior of the polymers (filler material).

Another embodiment of the present disclosure may include one or more of the following concepts:

A. A capsule for receiving and dosing high-viscosity materials comprising a housing, wherein the housing defines an interior chamber and has an opening for inserting a piston, and a delivery opening; and wherein the housing comprises the following sections:

a first housing section, which defines a first interior chamber section, wherein the first housing section has a first central longitudinal axis, a first end, and a second end;

a second housing section, which forms an exit nozzle, wherein the second housing section has a second central longitudinal axis, a first end, and a second end, and the second housing section defines an exit channel, which opens into the exit opening formed at the second end of the second housing section; and a transition section, whose first end is connected to the second end of the first housing section, and whose second end is connected to the first end of the second housing section;

wherein the first central longitudinal axis and the second central longitudinal axis intersect at an angle such that the transition section connects the first interior chamber section to the exit channel, wherein the transition between the transition section and the exit channel has a wall piece that is arranged transversely to the flow direction of the filler material.

B. The capsule of claim A, wherein the exit channel of the second housing section is formed like a cone and opens at an angle, especially an angle of about 1° to about 3°, to the exit opening.

C. The capsule of claim B, wherein the diameter of the interior chamber of the transition section decreases steadily from the first end to the second end and at a constant slope.

D. The capsule of claim A, wherein the taper angle is between about 50° and about 120°, especially between about 50° and about 70°.

Although not shown, the capsules and pistons as described above may act together in different combinations. The result is an improved delivery of the filler material with lower expression forces, greater reliability and lower requirements on the design of the capsule expression tools.

I claim:

1. A capsule for receiving and dosing high-viscosity materials comprising a housing, wherein the housing defines an interior chamber and has an opening for inserting a piston, and a delivery opening; and wherein the housing comprises:

a first housing section, which defines a first interior chamber section, wherein the first housing section has a first central longitudinal axis, a first end, and a second end;

a second housing section, which forms an exit nozzle, wherein the second housing section has a second central longitudinal axis, a first end, and a second end, and the second housing section defines an exit channel, which opens into the delivery opening formed at the second end of the second housing section; and a transition section, whose first end is connected to the second end of the first housing section, and whose second end is connected to the first end of the second housing section;

wherein the first central longitudinal axis and the second central longitudinal axis intersect at an angle, such that the transition section tapers between its first end section and its second end section in the form of an oblique truncated cone, the transition section has a taper angle that corresponds to the opening angle of the cone, and the taper angle is at least about 50°.

2. The capsule of claim 1, wherein the oblique truncated cone is arranged such that it is tilted at an angle relative to the first central longitudinal axis, with the angle being about 10° to about 20°.

3. The capsule of claim 1, wherein the transition section connects the first interior chamber section to the exit channel, and the transition between the transition section and the exit channel has a wall piece that is arranged transversely to a flow direction of a filler material.

4. The capsule of claim 3, wherein the wall piece is of an annular design and arranged substantially perpendicular to the second central longitudinal axis.

5. The capsule of claim 3, wherein the diameter of the interior chamber of the transition section decreases steadily from the first end of the transition section to an outer boundary of the wall piece and at a substantially constant slope.

6. The capsule of claim 3, wherein the second housing section connects to the transition section via the wall piece.

7. The capsule of claim 1, wherein the transition between the transition section and the exit channel has a flow edge.

8. The capsule of claim 1, wherein the exit channel of the second housing section is formed like a cone and opens at an angle, especially an angle of about 1° to about 3°, to an exit opening.

9. The capsule of claim 1, wherein a diameter of the interior chamber of the transition section decreases steadily from the first end of the transition section to the second end of the transition section and at a substantially constant slope.

10. The capsule of claim 1, wherein the taper angle is between about 50° and about 120°.

11. The capsule of claim 1, further comprising a piston for expressing material from the capsule, the piston having at least one end face and a scraper edge, wherein a transition surface of the end face, which is contiguous with the scraper edge, forms an angle of about 90° to about 120° with the longitudinal axis of the piston, wherein the angle is arranged such that, in the intended thrust direction for delivery of the filler material, the outward transition surface runs obliquely rearwards, further wherein a gap is arranged between the scraper edge and an inner wall of the first housing section of the capsule.

12. The capsule of claim 1, further comprising a piston for expressing material from the capsule, the piston having at least one end face and a scraper edge, wherein a transition surface of the end face, which is contiguous with the scraper edge, forms an angle of about 90° to about 120° with the longitudinal axis of the piston, wherein the angle is arranged such that, in the intended thrust direction for delivery of the filler material, the outward transition surface runs obliquely rearwards.

13. The capsule of claim 12, wherein the angle is between about 105° and about 120°.

14. The capsule of claim 12, wherein the scraper edge has an outer circumference, and wherein at least one elevation extends radially from the outer circumference.

15. The capsule of claim 14, wherein the at least one elevation creates a venting gap between the inner wall of the first housing section and the scraper edge.

16. A capsule for receiving and dosing high-viscosity materials comprising a housing, wherein the housing defines an interior chamber and has an opening for inserting a piston, and a delivery opening; and wherein the housing comprises:

a first housing section, which defines a first interior chamber section, wherein the first housing section has a first central longitudinal axis, a first end, and a second end;

a second housing section, which forms an exit nozzle, wherein the second housing section has a second central longitudinal axis, a first end, and a second end, and the second housing section defines an exit channel, which opens into the delivery opening formed at the second end of the second housing section; and a transition section, whose first end is connected to the second end of the first housing section, and whose second end is connected to the first end of the second housing section;

wherein the first central longitudinal axis and the second central longitudinal axis intersect at an angle such that the transition section connects the first interior chamber section to the exit channel, wherein the transition section tapers in the form of an oblique truncated cone, the transition section having a taper angle corresponding to the opening angle of the cone, and wherein the transition between the transition section and the exit channel has a wall piece that is arranged transversely to a flow direction through the capsule.

17. The capsule of claim 16, wherein the wall piece forms a complete annulus around the first end of the second housing section, the wall piece having a major face oriented substantially perpendicular to the second central longitudinal axis.

18. The capsule of claim 16, wherein the diameter of the interior chamber of the transition section decreases steadily from the first end of the transition section to the outer boundary of the wall piece and at a substantially constant slope.

19. The capsule of claim 16, wherein the second housing section connects to the transition section via the wall piece.

20. The capsule of claim 16, wherein the exit channel of the second housing section is formed like a cone and opens at an angle, especially an angle of about 1° to about 3°, to an exit opening.

21. The capsule of claim 16, wherein the taper angle is between about 50° and about 70°.

* * * * *